US011266448B2

(12) United States Patent
Rushton et al.

(10) Patent No.: US 11,266,448 B2
(45) Date of Patent: Mar. 8, 2022

(54) LOCKING INTRAMEDULLARY NAIL SYSTEM

(71) Applicants: Thomas E Rushton, Silver Spring, MD (US); Kevin R Desmond, Haverhill, MA (US); Mark J Warburton, High Point, NC (US)

(72) Inventors: Thomas E Rushton, Silver Spring, MD (US); Kevin R Desmond, Haverhill, MA (US); Mark J Warburton, High Point, NC (US)

(73) Assignee: Cidaris Ortho, Inc., High Point, NC (US)

( * ) Notice: Subject to any disclaimer, the term of this patent is extended or adjusted under 35 U.S.C. 154(b) by 250 days.

(21) Appl. No.: 16/537,083

(22) Filed: Aug. 9, 2019

(65) Prior Publication Data
US 2020/0046411 A1   Feb. 13, 2020

Related U.S. Application Data

(60) Provisional application No. 62/716,668, filed on Aug. 9, 2018.

(51) Int. Cl.
*A61B 17/72* (2006.01)
*A61B 17/88* (2006.01)
(Continued)

(52) U.S. Cl.
CPC ........ *A61B 17/7241* (2013.01); *A61B 17/725* (2013.01); *A61B 17/863* (2013.01);
(Continued)

(58) Field of Classification Search
CPC . A61B 17/7241; A61B 17/725; A61B 17/863; A61B 17/8863; A61B 17/888; A61B 17/1782; A61B 17/1725; A61B 17/7233; A61B 17/7283; A61B 17/86; A61B 17/8695; A61B 17/7258; A61B 17/7208; A61B 17/7225; A61B 17/7266;
(Continued)

(56) References Cited

U.S. PATENT DOCUMENTS 4,463,753 A * 8/1984 Gustilo ................ A61B 17/863
411/386
5,374,235 A * 12/1994 Ahrens .................. A61B 17/72
606/101
(Continued)

FOREIGN PATENT DOCUMENTS

| EP | 2590583 B1 | 2/2015 |
| ES | 2366053 T3 | 10/2011 |
| WO | 01/80751 A1 | 11/2001 |

*Primary Examiner* — Pedro Philogene
(74) *Attorney, Agent, or Firm* — Kimberly O Snead

(57) ABSTRACT

An intramedullary (IM) nail system for the fixation of fractured bones in a patient comprising a nail and compression screws. The length of the body is divided into a distal section and a proximal section with the distal section containing multiple interference sections having a diameter less or greater than that of the body. The threads adjacent the nail head have an apex generally greater than the diameter of the body. The compression screws are dimensioned to be inserted through the bone and contact the nail, pressing it against the bone canal. The nail, once inserted, lies below the surface of the bone.

19 Claims, 7 Drawing Sheets

(51) Int. Cl.
    *A61B 17/86* (2006.01)
    *A61B 17/56* (2006.01)
(52) U.S. Cl.
    CPC ......... *A61B 17/888* (2013.01); *A61B 17/8863* (2013.01); *A61B 2017/564* (2013.01)
(58) Field of Classification Search
    CPC .... A61B 2017/564; A61B 2017/00964; A61B 2017/00862
    See application file for complete search history.

(56) References Cited

U.S. PATENT DOCUMENTS

| | | |
|---|---|---|
| 6,793,659 B2 | 9/2004 | Putnam |
| 6,942,668 B2 | 9/2005 | Padget et al. |
| 7,250,053 B2 | 7/2007 | Orbay |
| 7,294,130 B2 | 11/2007 | Orbay |
| 7,763,021 B2 | 7/2010 | Cole et al. |
| 7,942,875 B2 | 5/2011 | Nelson et al. |
| 8,287,538 B2 | 10/2012 | Brenzel et al. |
| 8,287,541 B2 | 10/2012 | Nelson et al. |
| 8,454,605 B2 * | 6/2013 | Gradl ................. A61B 17/7283 606/62 |
| 8,460,294 B2 | 6/2013 | Overes |
| 8,715,325 B2 | 5/2014 | Weiner et al. |
| 9,220,544 B2 | 12/2015 | Matityahu et al. |
| 9,554,837 B2 | 1/2017 | Schonhardt et al. |
| 2005/0107791 A1 * | 5/2005 | Manderson ............ A61B 17/68 606/62 |
| 2011/0319946 A1 | 12/2011 | Levy et al. |
| 2016/0296263 A1 | 10/2016 | Champagne et al. |
| 2017/0112552 A1 | 4/2017 | Sinnott et al. |

\* cited by examiner

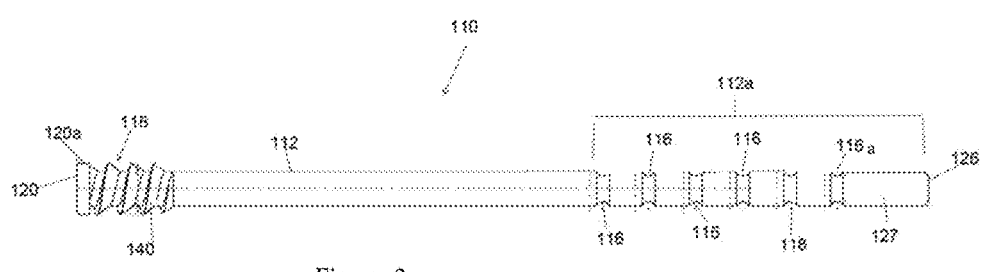
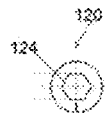
Figure 4
Figure 3
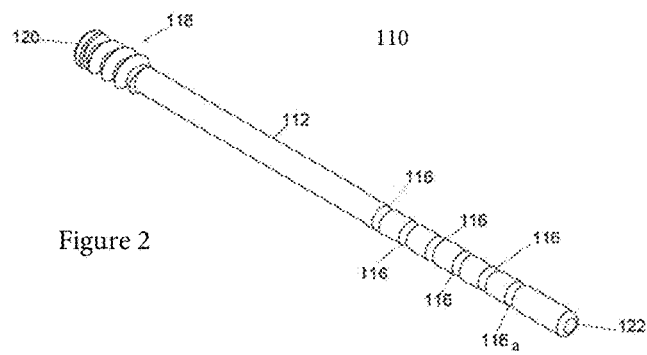
Figure 2
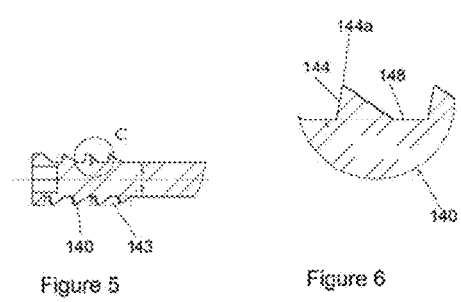
Figure 5
Figure 6

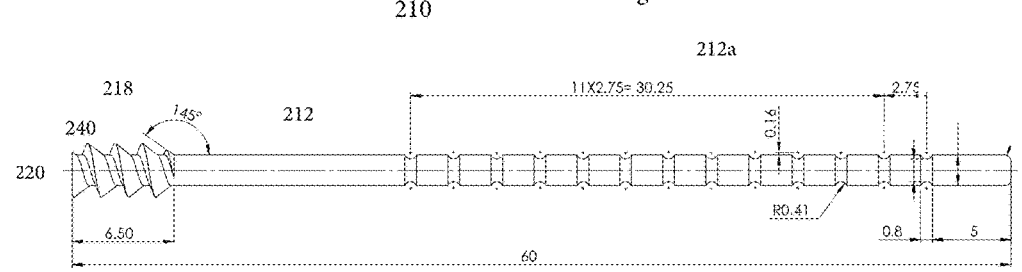
Figure 10
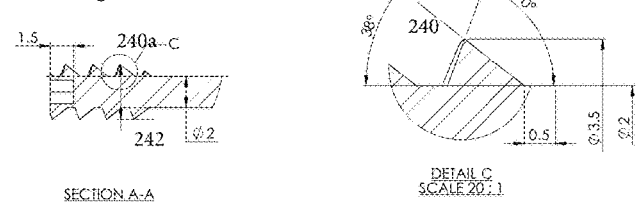
Figure 12
Figure 13
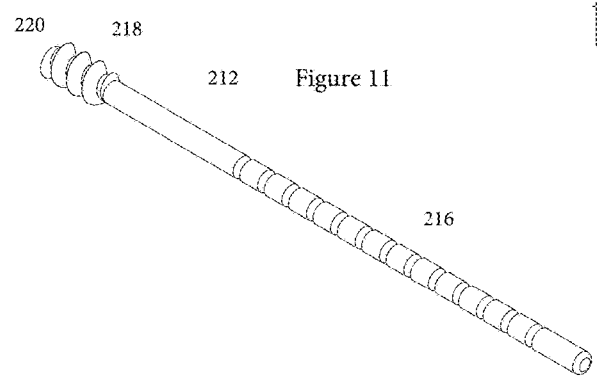
Figure 11
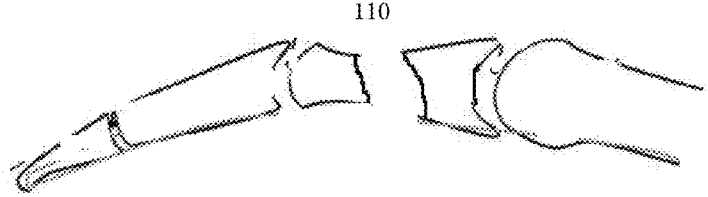
Figure 14
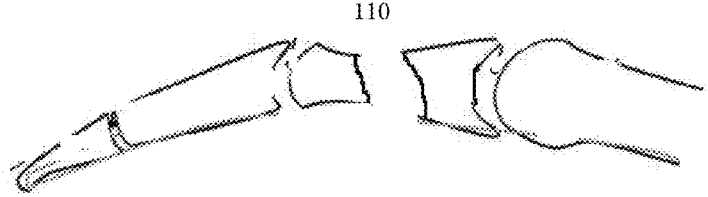
Figure 16

LOCKING INTRAMEDULLARY NAIL SYSTEM

FIELD OF THE INVENTION

The invention relates to an improved intramedullary nail (IM nail) for use in both small and large bones.

BACKGROUND OF THE INVENTION

It is well known that health care costs have risen dramatically partially as a result of equipment costs due to advancements in technology and the onslaught of malpractice lawsuits. One area that is commonly hit with the foregoing is orthopedics as broken bones are frequently the result of sports injuries, auto accidents, and household accidents.

Due to the fragility of the hand and foot bones, these are easily broken or crushed. Currently there are two primary options for fixation of small bone fractures. Open reduction internal fixation, usually reserved for severely fractured small bones, is a two-part surgery where the affected area is opened, and the bones put back into place. An internal fixation device, such as plates and screws, is then placed on the bone(s) to maintain them in place with the fixation device remaining in the patient. The other primary option is Intramedullary K-Wire of nail fixation. Here the surgeon runs a wire through the intramedullary canal, leaving the wire in place. After healing the wire is removed and the incision closed.

Both of the above procedures present complications resulting from infection or impairment and some require a second surgery.

SUMMARY OF THE INVENTION

An intramedullary (IM) nail system for the fixation of fractured bones in a patient comprising a nail and compression screws. The body of the nail has a proximal end with a head and threaded section adjacent thereto, a distal end, and a length therebetween. The length of the body is divided into a distal section and a proximal section with the distal section containing multiple interference sections having a diameter less or greater than that of the body. The threads of the threaded section have an apex generally greater than the diameter of the body. A driver receiving area is positioned within the head of the nail. The multiple compression screws are dimensioned to be inserted through the bone and contact the nail, pressing it against the bone canal. In some instances, a single compression screw can be used depending on its interaction with the interference sections which assist in maintaining the nail in the correct position.

The diameter of the head can be equal to the diameter of the body of the nail, equal to the apex of the threads, or between the two diameters.

When grooves are used for the interference sections, the outer diameter of the groove is about 15% the diameter of the body. As sizing examples for small bones, the nail body diameter can be between 1.6 mm (0.063 in) and 2.5 mm (0.098 in) with the groove diameter is between 1.1 mm (0.043 in) and 2.00 mm (0.078 in). The distal groove, or other interference section, is preferably spaced about 5 mm (0.196 in) from the distal end of the nail. The spacing between the grooves or interference sections should be between 2.75 mm (0.108 in) and 5 mm (0.196 in). The interference areas serve to assist in holding the compression screw in position.

The length of the nails can vary depending on end use; however, to avoid stocking numerous nails, a longer nail can be provided which can be cut to length prior to surgery. The dimensions of the body and the head place the nail below the plane of the outer surface of the bone, thereby avoiding joint interference. The nail can remain in the body or removed.

To secure the fracture a hole is drilled in an end of a first bone and, using a driver inserted into the driver receiving area, the nail is threaded through the bone canals. Once the fracture is positioned a hole is drilled at an angle, preferably perpendicular, to the nail and a compression screw inserted to contact the nail. If necessary additional compression screws can be inserted. The compression screw(s) press and maintain the nail adjacent to the bone canal.

BRIEF DESCRIPTION OF THE DRAWINGS

These and other objects, features, advantages and aspects of the present invention can be better understood with reference to the following detailed description of the preferred embodiments when read in conjunction with the appended drawing figures.

FIG. 2 is a perspective view of the IM nail in accordance with the invention;

FIG. 3 is a side view of the IM nail in accordance with the invention;

FIG. 4 is an end view of the IM nail illustrating the nail head and driver receiving area in accordance with the invention;

FIG. 5 is a detailed view of an example of the threaded section of the IM nail in accordance with the invention;

FIG. 6 is a detailed view of example threads for the threaded section in accordance with the invention;

FIG. 10 is a side view of the IM nail illustrating another example of dimensioning in accordance with the invention;

FIG. 11 is an isometric view of the nail of FIG. 10 in accordance with the invention;

FIG. 12 is a detailed view of an example of the threaded section of the IM nail in accordance with the invention;

FIG. 13 is a detailed view of example threads for the threaded section in accordance with the invention;

FIG. 14 is an example of an alternate interference area in accordance with the invention;

FIG. 16 is an example of the IM nail of the instant invention replacing missing bone in accordance with the invention.

DETAILED DESCRIPTION OF THE INVENTION

Definitions

Figure 1:
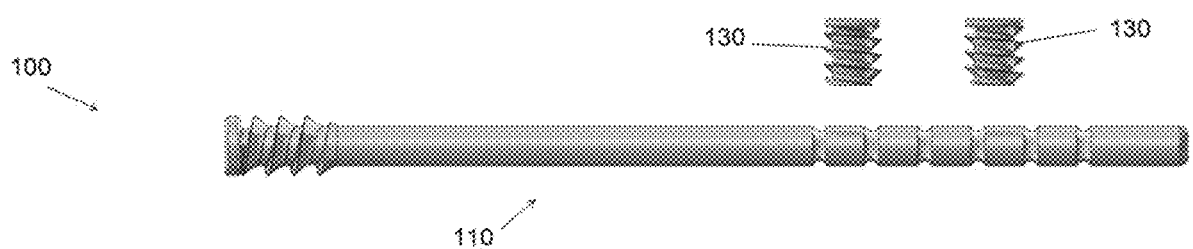
FIG. 1 is a side view of the IM nail system showing the IM nail and screws in accordance with the invention.
Figure 7:
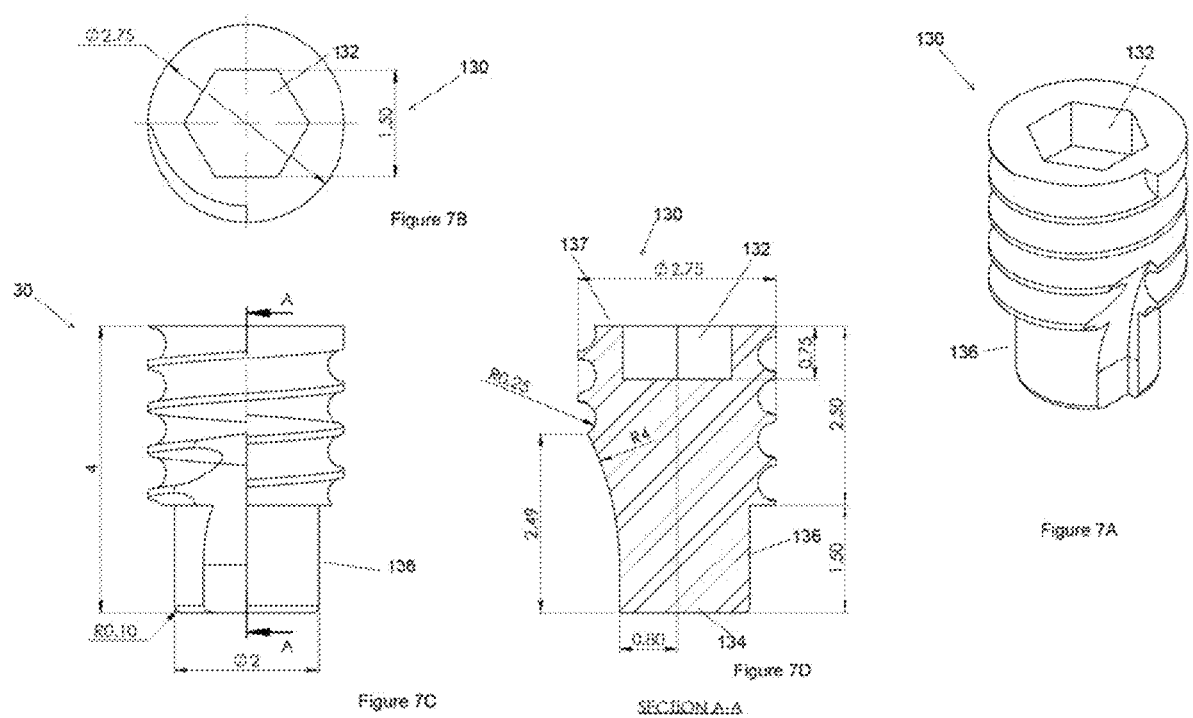
FIG. 7A is an isometric view of the driver receiving area and threads in accordance with the invention.
FIG. 7B is a top view of one embodiment of the compression driver receiving area in accordance with the invention.
FIG. 7C is side view of one embodiment of the compression screw in accordance with the invention.
FIG. 7D is cutaway view of one embodiment of the compression screw showing dimension in accordance with the invention.

As used herein the term "small bones" shall refer to metacarpal, metatarsal, phalanges, as well as bones of the wrist, forearm, and ankle.

As used herein the term "about" shall refer to a variation of +1-15%.

As used herein the term "fracture" shall refer to any type of a fracture, including but not limited to stable, open, compound, traverse, oblique or comminuted.

As used herein the term "interference area" shall refer to any spaced area along the distal portion of the nail that disrupts the smooth surface of the nail and provides grip or prevents slippage between the nail and the compression screw.

As used herein the term "screw" shall include any type of screw used for medical purposes, e.g. compression, or lag, screw.

The disclosed intramedullary (IM) nail system provides a unique product and method for the fixation of long bones, especially small bones, resulting from trauma to the area. The disclosed IM nail is capable of maintaining bone length in traumatic or comminuted fractures. The preservation of bone length is especially critical in the case of small bones due to the ease of fragmenting creating loss of bone length. In situations where bone is missing the bones are placed at the original length and the space between is replaced by the disclosed nail as illustrated in FIG. 16. The locking of the screws contacting the interference areas prevents rotation and longitudinal movement. All types of metacarpal fractures, including metacarpal neck fractures, can be treated as the IM nail can be inserted antegrade or retrograde of the fracture. In view of the rising costs of health care, it is advantageous to cut surgeon and operating room time which increasing patient safety and optimal recovery. The disclosed IM nail provides a safer, lower cost solution to the repair of small bones.

The disclosed IM nail system consists of a single use, unique locking IM nail and two, or more, distal locking screws that can remain in the patient, reducing the chance of infection and the need for secondary and corrective surgeries. The interaction between the locking screws and the nail prevents any rotation while preserving bone length. Due to its simplicity, eliminating multiple plates and screws, the number of failure points is reduced. The minimally invasive surgical technique reduces surgeon and operating time providing additional savings in standard hospital settings as well as reducing the strain on the hospital's sterilization department by eliminating the need for removal.

The disclosed IM nail system simplicity provides advantages for areas without access to large hospitals as the surgery is far less complex than prior art systems. The relative ease of insertion, reduced cost, permanency, minimal number of elements, and reduction of infection costs makes the disclosed IM nail system optimal for use in third world countries.

The disclosed IM nail system 100 can also be dimensioned for use on larger bones of the arm and legs as well as bones that require the head to be embedded within the bone. The benefits of the disclosed IM nail system are most evident in small bones where the bone size requires minimal nail size and generally eliminates the ability to use plates.

The IM nails can be manufactured from any biocompatible material that meets the strength requirements for the size being used. Example materials would be stainless steel, titanium, bioabsorbable polymers, polyether ether ketone, or other biocompatible materials.

The interference areas are illustrated in FIG. 1-14 as grooves as these provide additional advantages as noted below. The interference areas are used to provide a surface that will assist the compression screw in maintaining both rotation and longitudinal position. Therefore, any change in surface can be used and an example of an interference area surface is illustrated in FIG. 14 where the nail 350 has roughened area 352. The spacing and dimensioning taught herein are applicable regardless of the interference areas. Optimally the physician inserts the screws, with the assistance of fluoroscopy, to contact the interference areas at a right angle. In the event the compression screw contacts the center of the interference area, only one compression screw should be required. However, if the contact is on the edge or misses the interference area, a second compression screw can be required. The decision regarding additional screws is dependent upon the length of the nail and the type of fracture.

The grooves illustrated provide the advantages that in situations where the nail is to be cut to size prior to surgery, cutting at the grooves provides ease and additional accuracy. This is especially important with Boxer's fractures and other small hand bone repairs where exact dimensioning must be achieved. Additionally, grooves are clearer to see when using fluoroscopy.

The IM nail system 100 is illustrated in FIG. 1 wherein the nail 110 and screws 130 are illustrated. As can be seen from this figure, the number of elements is minimal. Although two screws 130 are illustrated herein, greater or fewer screws 130 can be used depending on the length of the nail 110. Once the screws 130 are in position against the nail 110 the nail 110 is pressed against the bone canal and locked into position. The locking action created by the screw 130 and nail 110 interaction is critical as it prevents rotation as well as any lateral movement ensuring length preservation.

In some applications, it can be advantageous to place additional grooves, or other interference areas, towards the distal end of the nail to ensure proper placement and securement.

FIG. 2 illustrates a perspective view of the nail 110 showing the placement of the grooves 116 along the body 112. In this figure the tip 122, head 120 and threads 118 are clearly illustrated.

In FIGS. 3-6 the interior of the IM nail 110 is illustrated in more detail and perspective views. The nail 110 body 112 has a nail head 120 at the proximal end and tip 122 at the distal end. In the dimensions illustrated in these figures, the nail head 120 has a slightly larger diameter than the body 112 and contains a driver receiving area 124 (FIG. 4). Adjacent the nail head 120 is the threaded portion 118 that leads to the body 112 that, toward the distal end, contains grooves 116.

The dimensioning of the IM nail head 120 is critical as, once inserted, generally at the end of a small bone, the head is below the surface adjacent the end of the small bone requiring stabilization. This placement below the surface reduces the chances of infection while still enabling removal if necessary. Two dimensions are illustrated herein, one with the head 120 having a diameter equal to that of the threads 118 and another (FIG. 10), having the head 220 the diameter of the body 212. These are examples and other dimensioning can be used that meets with the criteria of the disclosed system.

Adjacent to the IM nail head 120 and having the same diameter as the nail head 120, is the threaded portion 118 that serves to secure the distal end of the IM nail 110. The threads 140 of the threaded portion 118 are illustrated in more detail in FIGS. 5 and 6. As seen in FIGS. 5 and 6, FIG. 6 illustrating the detail C of FIG. 5, the apex 144a of the thread 144 is on the same plane as the outer periphery 120a of the nail head 120. This maintains the maximum profile of the threaded portion 118 on the same plane as the periphery 120a, thereby enabling the threaded portion 118 to be maintained under the skin. The distance 143 between the apex 144a of the threads is about 3.0 cm (0.118 in).

The example configuration of the threads 144, as illustrated in FIG. 6, are course cut to enable the IM nail 110 to be screwed in with three full rotations. In this example configuration the nearly 90° cut of the thread 144 provides extra hold. Other thread configurations, one of which is illustrated in FIG. 13, will be evident to those skilled in the art.

At the distal portion 112a of the body 112 contains multiple grooves 116. In the illustrated embodiment the body 112 has a diameter of 1.75 mm (0.068 in), the grooves 116 are approximately 0.25 mm (0.01 in) deep leaving about a 1.5 mm (0.059 in) minimum diameter. In this example the diameter of the body 110 and the interior diameter of the grooves 116 is a difference of approximately 15%. As the diameter of the body 110 can be increased or decreased, depending on end use, care must be taken to ensure that the depth of the grooves 116 are not so great as to weaken the strength of the IM nail. An example of the dimensioning is a nail having an outer diameter of about 1.6 mm (0.063 in) having grooves with an outer diameter of about 1.1 mm (0.043 in). Another example is about a 3.0 mm (0.118 in) outer diameter with about 2.6 mm (0.102 in) groove diameter. These, along with FIGS. 10-14, are examples of nail dimensions for use with small long bones, and other dimensions for use with larger long bones will be evident to those in the orthopedic arts based on the teaching of the instant disclosure. In most applications the outer diameter (OD) of the groove will be about 80% of the OD of the nail. The foregoing sizes are optimal for use in small bones and other sizes, as well as dimensioning for use with larger bones will be evident to those skilled in the art.

Although the example illustrated in FIG. 3 has six (6) grooves 116, the number can change accordingly to the length and end use of the IM nail 110, as illustrated in another example hereinafter. The distal groove 116a should be at least 5 mm (0.196 in) from the distal end 126 of the nail 110 to form the lead section 127. The lead section 127 has the same diameter as the ungrooved portion body 112 of the nail 110 to provide the strength of lead through the bone canal. The grooves, or interference areas, are generally equally spaced at about 2.75 mm (0.108 in) to about 5 mm (0.196 in) intervals to ensure engagement with the distal screws, although spacing can vary depending on the configuration of the nail. For example, when using the nail dimensions illustrated in FIGS. 10 and 11, a shorter distance between interference areas can be preferable to provide a sufficient number of areas for contact once the nail is cut.

Figure 15:
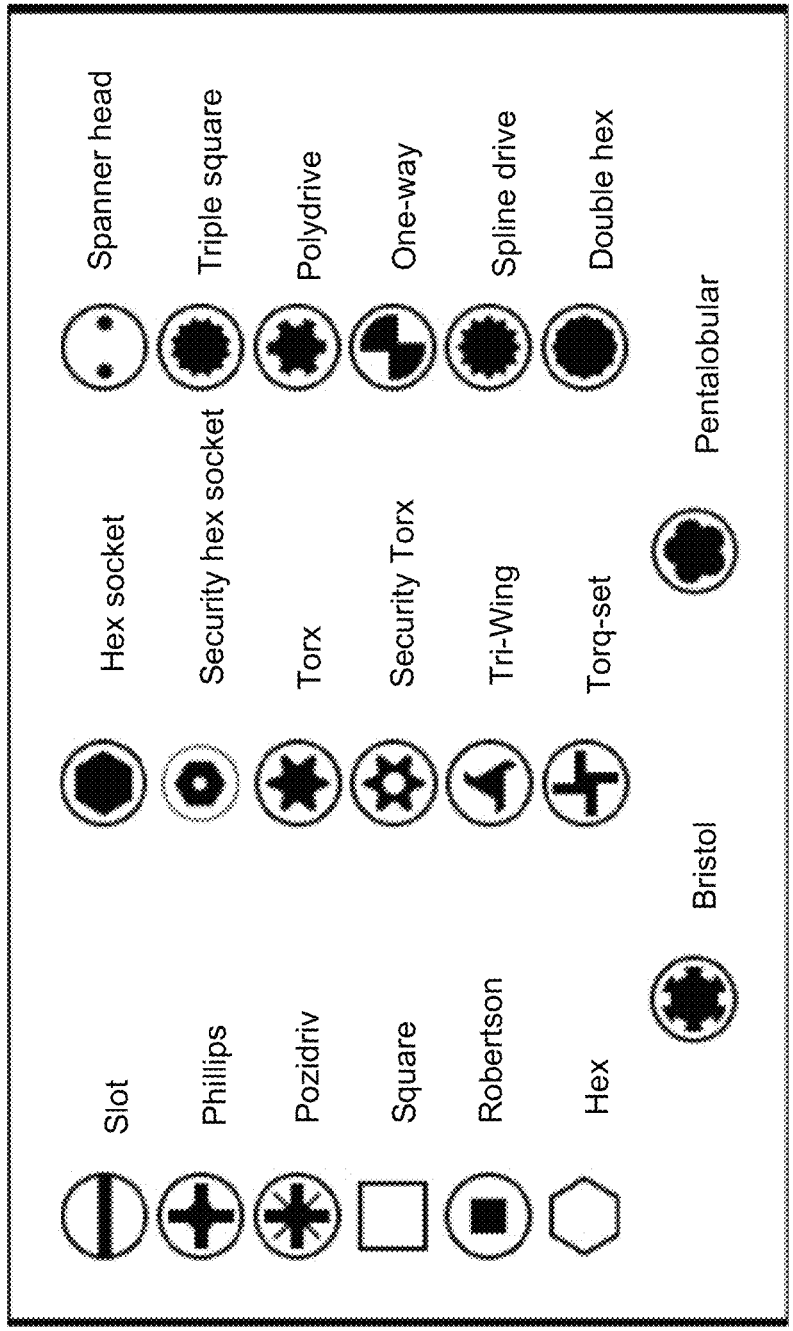
FIG. 15 is a standard chart of driver tips to which the driver receiving area can be configured for compatibility in accordance with the Invention.

The screws 130 are configured to interact with the grooves 116 of the IM nail 110. It is preferable that the driver receiving area 132 (FIG. 7A) of the screws 130, generally 1.5 mm (0.059 in), is the same configuration and dimension as that of the driver receiving area 124 of the nail for convenience. It should be noted that this is an issue of convenience and not necessity and that the driver receiving area 124 can vary with manufacturing preference and nail size. For example, the driver receiving area 124 can be a hex, star tip, pozi, square, or other configuration that provides a secure interaction between the driver and the driver receiving area 124. FIG. 15 illustrates a standard chart of driver tip configurations, any of which can be used in the disclosed.

Figure 8:
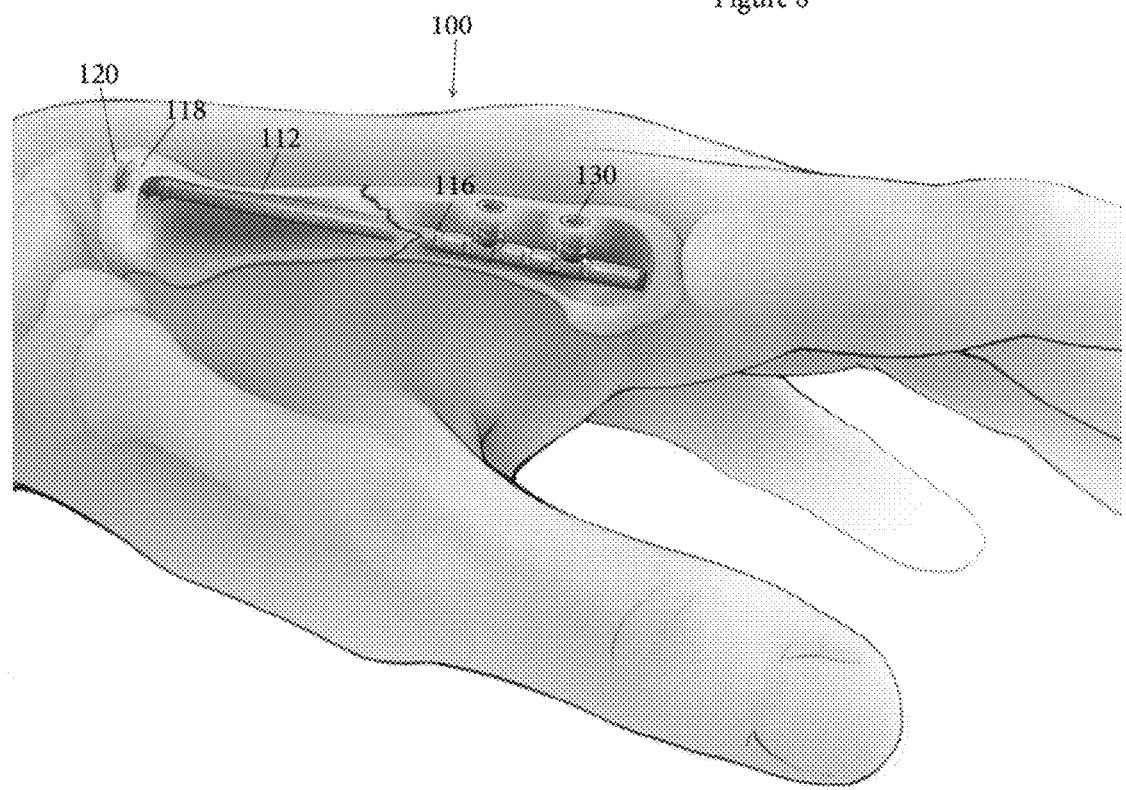
FIG. 8 is a cutaway view of the IM nail in position within a small bone in accordance with the invention.

An example screw 130 is illustrated in FIGS. 7A-7D. In these Figures the recess of the driver receiving area 132 is clearly illustrated in Figured 7A, 7B and 7D. The screw 130 is used with all nails with the only change being extending the length. As seen in the example dimensions of FIG. 7B the driver receiving area 132 of this example has a depth of 0.75 mm (0.029 in) with a width of 1.50 mm (0.059 in). In a screw 130 having a length of 4.0 mm (0.157 in) and a contact base 134 width of 1.60 mm (0.062 in), the threaded head has a width of 2.75 mm (0.108 in). In this example, the threaded portion is 2.50 mm (0.098 in) leaving a body length 136 of 1.50 mm (0.059 in). The body length 136 must be sufficient to contact the inserted nail 110 while maintaining the screw head 137 at the surface of the bone, as illustrated in FIG. 8. In these views, the IM nail 110 is dimensioned for use in small bones.

In FIG. 8 the IM nail system 100 is illustrated inserted into a metacarpal. As can be seen in this figure, the IM nail head 120 is fully inserted within the proximal end of the bone and prevented from backing out by the threaded portion 118. The screws 130 are inserted at an angle to the nail, contacting, the nail body 112, maintaining the distal end 126 in position. Although it is preferable that the screws 130 interact directly with the grooves 116, this cannot always be possible, and the configuration illustrated in FIG. 8 is the more common configuration. The pressure created by the screws 130 forces the nail 112 into contact with the bone canal. Additionally, in complicated fractures requiring at least two compression screws 130, the screws will act against each other pinning the nail securely in place. As illustrated in this Figure, once inserted all elements of the IM nail system are below the skin.

Figure 9A:
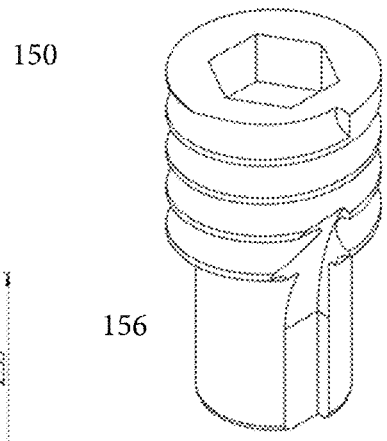
FIG. 9A is an isometric view of another dimensioning example of the compression screw in accordance with the invention.
Figure 9B:
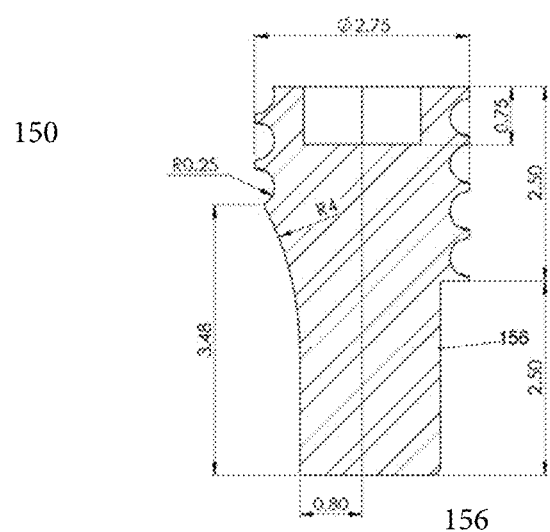
FIG. 9B is cutaway view of another dimensioning example of the compression screw showing dimension in accordance with the invention.

In FIGS. 9A and 9B, the example screw 150 has the same dimensions as the screw 130 with the exception of the body length 156 which has been extended to 2.5 mm (0.0984 in). This extended length enables the system 100 to be used in larger bones.

The IM nail 200 of FIGS. 10-14 illustrates additional dimensioning examples. The length of the nail 210 has been extended to about 60 mm (2.36 in) with an increased distal portion 212a of the body 212 being provided with grooves 216. That longer nail 210 gives the ability to cut the nail 210 to size where a shorter nail is required but not necessarily available. The nail 210 can be cut at, or between, the grooves 216. The ability to cut the nail 210 to size just prior to surgery reduces the expense of stocking multiple sized nails as well as manufacturing and shipping costs. This is especially advantageous in rural settings where finances and/or space makes stocking various sized nails unfeasible.

As disclosed heretofore with respect to FIGS. 2 and 3, the nail 210 body 212 has a nail head 220 at the proximal end and tip 222 at the distal end. The nail head 220, in contrast to the nail head 120, has a diameter equal to that of the body 212 thereby enabling the nail to be flush with, or below, the bone surface of smaller bones. This especially applies to setting what is referred to boxer's fractures, the breaking of the fourth and/or fifth metacarpal bone near the knuckle. The nail head 220 contains the device receiving area which, as described heretofore, can have any configuration compatible with the chosen drivers.

The dimensioning of the IM nail head 220, once inserted at end of a small bone, places the head 220 below the plane of the outer surface of the bone requiring stabilization. This placement below the surface, in addition to the advantages described heretofore, ensures there is no interference with the joint. Further, seating the nail 220 within the insertion point eliminates joint protrusion or impingement whether the insertion is antegrade or retrograde. This is especially critical since metatarsal insertion can only be performed retrograde.

Adjacent to the IM nail head 220 is the threaded portion 218 that serves to secure the distal end of the IM nail 210. The threads 240 of the threaded portion 218 are illustrated in more detail in FIGS. 12 and 13 wherein alternate dimensioning to that of FIGS. 5 and 6 is illustrated. In FIG. 13 the thread pitch is slightly greater, bringing the pitch to approximately 70 degrees from normal in comparison to the 80 degrees of FIG. 6. Additionally, in the example dimensioning of FIG. 12, the distance 242 between the apex 240*a* of the threads 240 is 3.5 cm (0.137 in) in contrast to the 3.0 cm (0.118 in) of distance 143 illustrated in FIG. 5. For simplicity and cost of manufacturing, maintaining the threads apex at a consistent size for all small bone nails is preferable however this does not preclude varying the apex dimensions based on a predetermined criteria such as length or diameter. For IM nails use on large long bones the threads would, depending upon nail dimensioning and end use, require enlarging. Selecting the correct dimensions for large long bones can be done by those skilled in the art based upon the teachings herein.

Insertion Procedure.

With an awl or drill, a hole is made at the proximal or distal end (antegrade or retrograde) of the bone. With a driver dimensioned to fit the driver receiving area, such as a stick fit driver, the IM Nail is threaded through the fracture. Fluoroscopy, or other applicable methods, is used to direct the insertion through the bone.

Once the bones are in place and the fracture is reduced around the nail, one or two holes are drilled at the distal end of the small bone, approximately perpendicular to the nail, so that a screw can be placed to contact the bone. The screw serves as a compression screw that interfaces with the nail body and groove in such a way to hold the nail firmly against the intramedullary canal. As with the nail, the screws can be manufactured from a bio-absorbable composite, stainless, titanium or other biocompatible material. Once the bone has healed, the IM nail can be removed or remain within the bone with the screws, if bio-absorbable, having been absorbed in the small bone. Whether or not the nail is removed, the screws will remain in the bone.

Since the IM nail system 100, using either nail 110 or nail 210, especially when used for small bones, is a compact system, sterile units, along with a small driver, awl, and probes, can be easily shipped to rural areas.

The use of the terms "a" and "an" and "the" and similar references in the context of this disclosure (especially in the context of the following claims) are to be construed to cover both the singular and the plural, unless otherwise indicated herein or clearly contradicted by context. An methods described herein can be performed in any suitable order unless otherwise indicated herein or otherwise clearly contradicted by context. The use of any and all examples, or exemplary language (e.g., such as, preferred, preferably) provided herein, is intended merely to further illustrate the content of the disclosure and does not pose a limitation on the scope of the claims. No language in the specification should be construed as indicating any non-claimed element as essential to the practice of the present disclosure.

Multiple embodiments are described herein, including the best mode known to the inventors for practicing the claimed invention. Of these, variations of the disclosed embodiments will become apparent to those of ordinary skill in the art upon reading the foregoing disclosure. The inventors expect skilled artisans to employ such variations as appropriate (e.g., altering or combining features or embodiments), and the inventors intend for the invention to be practiced otherwise than as specifically described herein.

Accordingly, this invention includes all modifications and equivalents of the subject matter recited in the claims appended hereto as permitted by applicable law. Moreover, any combination of the above described elements in all possible variations thereof is encompassed by the invention unless otherwise indicated herein or otherwise clearly contradicted by context.

The use of individual numerical values are stated as approximations as though the values were preceded by the word "about", "substantially", or "approximately." Similarly, the numerical values in the various ranges specified in this application, unless expressly indicated otherwise, are stated as approximations as though the minimum and maximum values within the stated ranges were both preceded by the word "about", "substantially", or "approximately." In this manner, variations above and below the stated ranges can be used to achieve substantially the same results as values within the ranges. As used herein, the terms "about", "substantially", and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about", "substantially", or "approximately" will serve to broaden a particular numerical value or range. Thus, as a general matter, "about", "substantially", or "approximately" broaden the numerical value. Also, the disclosure of ranges is intended as a continuous range including every value between the minimum and maximum values plus the broadening of the range afforded by the use of the term "about", "substantially", or "approximately". Thus, recitation of ranges of values herein are merely intended to serve as a shorthand method of referring individually to each separate value falling within the range, unless otherwise indicated herein, and each separate value is incorporated into the specification as if it were individually recited herein. To the extent that determining a given amount of variation of some the factors such as the criticality of the slit patterns, paper width differential pre- and post expansion, paper weights and type, as well as other considerations known to those of skill in the art to which the disclosed subject matter is most closely related or the art relevant to the range or element at issue will have on the performance of the claimed subject matter, is not considered to be within the ability of one of ordinary skill in the art, or is not explicitly stated in the claims, then the terms "about", "substantially", and "approximately" should be understood to mean the numerical value, plus or minus 10%.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. An intramedullary (IM) nail system for the fixation of fractured bones in a patient comprising:
    a nail and multiple screws, said nail having:
        a body having:
            a proximal end,
            a distal end,
            a length extending between said proximal end and said distal end, said length having a proximal section and, a distal section,
            a first diameter of said body extending from said proximal end to said distal end,
            a threaded section at said proximal section with threads having an apex greater than said first diameter, and
            multiple interference areas in said distal section, said multiple interference areas providing a disturbance in said length and having a second diameter less than said first diameter; and
        a head and driver receiving area adjacent to said proximal end of said body;
    wherein said nail is inserted into an end of a first bone and extends into a second bone,
    wherein said nail is maintained within said first bone by said threads,
    wherein said nail is maintained within said second bone by said screws inserted into said second bone at an angle to said nail to contact at least one of said multiple interference areas and lock said nail against bone canal to prevent rotation and longitudinal movement, and
    wherein said head lies below a plane of a surface of the bone.

2. The nail system of claim 1 wherein said interference areas are grooves extending around a circumference of said body and creating a groove diameter within said body.

3. The nail system of claim 1 wherein said head has a diameter equal to said body diameter.

4. The nail system of claim 1 wherein said head has a diameter equal to said apex of said threads.

5. The nail system of claim 2 wherein said groove diameter is about 15% of said body diameter.

6. The nail system of claim 1 wherein said body diameter is between 1.6 mm (0.063 in) and 2.5 mm (0.098 in).

7. The nail system of claim 2 wherein said groove diameter is between 1.1 mm (0.043 in) and 2.00 mm (0.078 in).

8. The nail system of claim 1 wherein one of said multiple interference areas is a distal groove spaced from said distal end at least 5 mm (0.196 in).

9. The nail system of claim 1 wherein said multiple interference areas are spaced from adjacent said multiple interference areas at least 2.75 mm (0.108 in).

10. The nail system of claim 1 wherein said distal section is cut to a predetermined length prior to surgery.

11. The nail system of claim 1 wherein said nail system is retained within said patient.

12. The nail system of claim 1 wherein said nail replaces bone missing between two bones due to fragmentation.

13. The nail system of claim 11 wherein said head has a diameter equal to said body diameter.

14. The nail system of claim 11 wherein said head has a diameter equal to said apex of said threads.

15. The nail system of claim 11 wherein said body diameter is between 1.6 mm (0.063 in) and 2.5 mm (0.098 in) and said groove diameter is between 1.1 mm (0.043 in) and 2.00 mm (0.078 in).

16. The nail system of claim 1 wherein said distal section is cut to a predetermined length.

17. An intramedullary (IM) nail system for the fixation of fractured bones in a patient comprising:
    a nail and multiple screws, said nail having:
        a body having:
            a proximal end,
            a distal end,
            a length extending between said proximal end and said distal end, said length having a proximal section and a distal section,
            a body having a first diameter extending from said proximal end to said distal end,
            a threaded section, at said proximal section with threads having an apex greater than said first diameter, and
            multiple grooves in said distal section, said multiple grooves having a second diameter about a groove diameter of 15% less than said first diameter and spaced from said distal end and from adjacent grooves at least 5 mm (0.196 in),
    wherein said nail is inserted into an end of a first bone and extends into a second bone to retain bone length,
    wherein said nail is maintained within said first bone by said threads, and
    wherein said nail is maintained within said second bone by said screws inserted into said distal end at an angle to said nail to contact at least one of said multiple grooves and lock said nail against bone canal to prevent rotation and longitudinal movement.

18. The nail system of claim 17 wherein said nail system is retained within said patient.

19. A method of securing a fracture in a patient and retain bone length using a nail system having a nail and retaining screws, comprising the steps of:
    drilling a hole into a first bone and into a second bone,
    inserting a driver into a driver receiving area in a head of said nail,
    threading said nail through said fracture into said first bone and said second bone, until said head is recessed within said fracture,
    reducing said fracture around said nail,
    drilling at least one hole at an angle to a distal end said nail through said bone,
    inserting a compression screw through said at least one hole to contact said nail,
wherein said compression screw presses said nail against a canal of said bone and said head lies below the plane of the surface of said bone.

* * * * *